United States Patent
Casero et al.

(10) Patent No.: US 9,527,805 B2
(45) Date of Patent: Dec. 27, 2016

(54) SMALL MOLECULES AS EPIGENETIC MODULATORS OF LYSINE-SPECIFIC DEMETHYLASE 1 AND METHODS OF TREATING DISORDERS

(76) Inventors: Robert A. Casero, Glen Arm, MD (US); Ian Bytheway, Nathan (AU); Patrick M. Woster, Charleston, SC (US)

( * ) Notice: Subject to any disclaimer, the term of this patent is extended or adjusted under 35 U.S.C. 154(b) by 189 days.

(21) Appl. No.: 13/821,962
(22) PCT Filed: Sep. 12, 2011
(86) PCT No.: PCT/US2011/051186
§ 371 (c)(1), (2), (4) Date: Sep. 25, 2013
(87) PCT Pub. No.: WO2012/034116
PCT Pub. Date: Mar. 15, 2012

(65) Prior Publication Data
US 2014/0011857 A1 Jan. 9, 2014

Related U.S. Application Data
(60) Provisional application No. 61/381,739, filed on Sep. 10, 2010.

(51) Int. Cl.
C07C 237/16 (2006.01)
C07C 211/53 (2006.01)
C07C 259/14 (2006.01)
C07C 275/24 (2006.01)
C07C 335/12 (2006.01)
C07D 209/48 (2006.01)

(52) U.S. Cl.
CPC .......... *C07C 237/16* (2013.01); *C07C 211/53* (2013.01); *C07C 259/14* (2013.01); *C07C 275/24* (2013.01); *C07C 335/12* (2013.01); *C07D 209/48* (2013.01)

(58) Field of Classification Search
None
See application file for complete search history.

(56) References Cited

U.S. PATENT DOCUMENTS

| 4,041,072 A * | 8/1977 | Fauran et al. ................. 564/164 |
| 5,106,973 A * | 4/1992 | Stokbroekx .......... C07D 237/20 544/238 |
| 2009/0291945 A1 | 11/2009 | Unoki et al. |

FOREIGN PATENT DOCUMENTS

| WO | WO2005016870 | * 2/2005 | ........... C07C 235/38 |
| WO | 2010151791 A1 | 12/2010 | |

OTHER PUBLICATIONS

Oger, F., et al., Biological and Biophysical Properties of the Histone Deacetylase Inhibitor Suberoylanilide Hydroxamic Acid Are Affected by the Presence of Short Alkyl Groups on the Phenyl Ring, Journal of Medicinal Chemistry (Mar. 11, 2010), 53(5). pp. 1937-1950.

Moquist P.N. et al, Enantoselecve Addton of Boonaes to Chomene Aceas Caayzed by a Chial Bonsed Acid/Lewis Acid System, Angewandte Chemie, International Edition (Aug. 18, 2010), 49(39), pp. 7096-7100.

Duguet, N. et al., Chiral relay in NHC-mediated asymmetric betalactam synthesis II; asymetry from NHCs derived from acyclic 1,2-diamines, Tetrahedron: Asymmetry (Mar. 30, 2010), 21(5), pp. 601-616.

Roche, S.P. et al., Synthesis of 1,2-diamines under environmentally benign conditions: application for the preparation of imidazolinium salts, Tetrahedron Letters (Mar. 3, 2010), 51(9), pp. 1265-1268.

Pareek, A.K. et al., Aa convenient route for the synthesis and characterization of novel substituted azo-coumarins and Schiff's bases, Oriental Journal of Chemistry (2009), 25(4), pp. 1149-1152.

Akiyama, K. et al., Stereoisomerically Pure Trisubstituted Vinylaluminum Reagents and their Utility in Copper-Catalyzed Enantioselective Synthesis of 1,4-Dienes Containing Z or E Alkenes, Angewandte Chemie, International Edition, Supporting Information, Part A, (Jan. 8, 2010), 49(2), pp. 419-423.

Durran, S.E. et al., Flexible .kappa.4-PNN'O-tetradentate ligands: synthesis, complexation and structural studies, Dalton Transactions (Jul. 20, 2010), 39(30), pp. 7136-7146.

Link, N.P. et al., An efficient synthesis of N-arylputrescines and cadaverines, Synlett (2009), (5), pp. 751-754.

International Search Report for PCT/US2011/051186, Apr. 24, 2012 (5 pages).

Written Opinion for PCT/US2011/051186, Apr. 24, 2012 (12 pages).

* cited by examiner

*Primary Examiner* — Clinton Brooks
(74) *Attorney, Agent, or Firm* — Mintz Levin Cohn Ferris Glovsky and Popeo, P.C.; Peter F. Corless, Esq.; Daniel W. Clarke

(57) ABSTRACT

The invention provides for novel compounds which are inhibitors of lysine-specific demethylase 1 (LSD1) such as those according to Formula II. Such compounds may be used to treat disorders, including cancer.

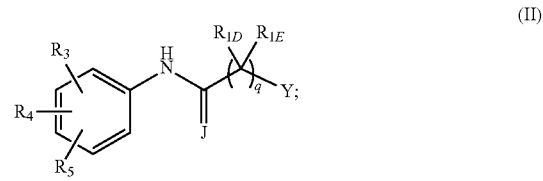

(II)

7 Claims, No Drawings

SMALL MOLECULES AS EPIGENETIC MODULATORS OF LYSINE-SPECIFIC DEMETHYLASE 1 AND METHODS OF TREATING DISORDERS

CROSS-REFERENCE TO RELATED APPLICATIONS

The present application is a 35 U.S.C. §371 U.S. national stage entry of International Application PCT/US2011/051186 (WO 2012/034116) having an International filing date of Sep. 12, 2011 which claims the benefit of U.S. Provisional application No. 61/381,739, filed on Sep. 10, 2010. The entire contents of the aforementioned applications are incorporated herein by reference.

TECHNICAL FIELD

The invention provides for small molecule compounds which are inhibitors of lysine-specific demethylase 1 (LSD1). Such compounds may be used to treat disorders, including cancer.

BACKGROUND OF THE INVENTION

Chromatin architecture is a key determinant in the regulation of gene expression, and this architecture is strongly influenced by post-translational modifications of histones (Marks, P. A.; et al. *Curr Opin Oncol* 2001, 13 (6), 477-483; Luger, K.; et al. *Nature* 1997, 389 (6648), 251-260). Histone protein tails contain lysine residues that interact with the negative charges on the DNA backbone. These lysine-containing tails, consisting of up to 40 amino acid residues, protrude through the DNA strand, and act as a site for post-translational modification of chromatin, allowing alteration of higher order nucleosome structure (Jenuwein, T.; Allis, C. D. *Science* 2001, 293 (5532), 1074-1080). Multiple post-translational modifications of histones can mediate epigenetic remodeling of chromatin, with acetylation being the best characterized process (Johnstone, R. W. *Nat Rev Drug Discov* 2002, 1 (4), 287-299). Transcriptional repression is associated with specific CpG island DNA methylation and recruitment of histone deacetylases (HDACs) to gene promoters that cooperate in the epigenetic silencing of specific genes (Herman, J. G.; Baylin, S. B. *N Engl J Med* 2003, 349 (21), 2042-2054; Robertson, K. D. *Oncogene* 2001, 20 (24), 3139-3155). Normal mammalian cells exhibit an exquisite level of control of chromatin architecture by maintaining a balance between histone acetyltransferase (HAT) and HDAC activity (Shogren-Knaak, M.; et al. *Science* 2006, 311 (5762), 844-847).

In cancer, CpG island DNA promoter hypermethylation in combination with other chromatin modifications, including decreased activating marks and increased repressive marks on histone proteins 3 and 4, have been associated with the silencing of tumor suppressor genes (Baylin, S. B.; Ohm, J. E. *Nat Rev Cancer* 2006, 6 (2), 107-116). The important role of promoter CpG island methylation and its relationship to covalent histone modifications has recently been reviewed (Jones, P. A.; Baylin, S. B. *Cell* 2007, 128 (4), 683-692). The N-terminal lysine tails of histones can undergo numerous posttranslational modifications, including phosphorylation, ubiquitination, acetylation and methylation (Johnstone, R. W. *Nat Rev Drug Discov* 2002, 1 (4), 287-299; Shi, Y.; et al. *Cell* 2004, 119 (7), 941-953; Whetstine, J. R.; et al. *Cell* 2006, 125 (3), 467-481). To date, 17 lysine residues and 7 arginine residues on histone proteins have been shown to undergo methylation, and lysine methylation on histones can signal transcriptional activation or repression, depending on the specific lysine residue involved (Bannister, A. J.; et al. *Nature* 2005, 436 (7054), 1103-1106; Kouzarides, T. *Curr Opin Genet Dev* 2002, 12 (2), 198-209; Martin, C.; et al. *Nat Rev Mol Cell Biol* 2005, 6 (11), 838-849; Zhang, Y.; Reinberg, D. *Genes Dev* 2001, 15 (18), 2343-2360). All known histone lysine methyltransferases contain a conserved SET methyltransferase domain, and it has been shown that aberrant methylation of histones due to SET domain deregulation is linked to carcinogenesis (Schneider, R.; et al. *Trends Biochem Sci* 2002, 27 (8), 396-402). Histone methylation, once thought to be an irreversible process, has recently been shown to be a dynamic process regulated by the addition of methyl groups by histone methyltransferases and removal of methyl groups from mono- and dimethyllysines by lysine specific demethylase 1 (LSD1), and from mono-, di, and trimethyllysines by specific Jumonji C (JmjC) domain-containing demethylases (Shi, Y.; et al. *Cell* 2004, 119 (7), 941-953; Whetstine, J. R.; et al. *Cell* 2006, 125 (3), 467-481; Tsukada, Y.; Zhang, Y. *Methods* 2006, 40 (4), 318-326; Huarte, M.; et al. *J Biol Chem* 2007.). Additional demethylases in the JmjC demethylase class are continuing to be identified (Liang, G.; et al. *Nat Struct Mol Biol* 2007, 14 (3), 243-245; Secombe, J.; et al. *Genes Dev* 2007, 21 (5), 537-551. Recent evidence suggests that LSD1 is required for maintenance of global DNA methylation, indicating that the LSD1-mediated demethylation is a general mechanism for transcriptional control (Wang, J.; et al. *Nat Genet* 2009, 41 (1), 125-129).

A key positive chromatin mark found associated with promoters of active genes is histone 3 dimethyllysine 4 (H3K4me2) (Liang, G., et al. *Proc Natl Acad Sci USA* 2004, 101 (19), 7357-7362; Schneider, R.; et al. *Nat Cell Biol* 2004, 6 (1), 73-77). LSD1, also known as BHC110 and KDM1, catalyzes the oxidative demethylation of histone 3 methyllysine 4 (H3K4me1) and H3K4me2, and is associated with transcriptional repression. H3K4me2 is a transcription-activating chromatin mark at gene promoters, and demethylation of this mark by LSD1 may prevent expression of tumor suppressor genes important in human cancer (Huang, Y.; et al. *Proc Natl Acad Sci USA* 2007, 104 (19), 8023-8028). Chemical compounds targeting epigenetic modifications such as LSD1 can selectively kill cancer cells. Thus, LSD1 is emerging as an important new target for the development of specific inhibitors as a new class of antitumor drugs (Stavropoulos, P.; Hoelz, A. *Expert Opin Ther Targets* 2007, 11 (6), 809-820).

To date, only a few existing compounds have been shown to act as inhibitors of LSD1. The active site structure of LSD1 has considerable sequence homology to monoamine oxidases A and B (MAO A and B), and to $N^1$-acetylpolyamine oxidase (APAO) and spermine oxidase (SMO) (Shi, Y.; et al. *Cell* 2004, 119 (7), 941-953; Lee, M. G.; et al. *Chem Biol* 2006, 13 (6), 563-567; Schmidt, D. M.; McCafferty, D. G. *Biochemistry* 2007, 46 (14), 4408-4416). Thus an appreciated problem in the art is that the few known LSD1 inhibitors are MAO, APAO or SMO inhibitors or derivatives thereof. It has been shown that classical MAO inhibitors such as phenelzine and tranylcypromine (Parnate®, Jatrosom®) inactivate nucleosomal demethylation by the recombinant LSD1/CoRest complex, and increase global levels of H3K4me2 in the P19 cell line. The synthetic substrate analogue aziridinyl-K4H3$_{1-21}$ reversibly inhibited LSD1 with an IC$_{50}$ of 15.6 μM, while propargyl-K4H3$_{1-21}$ produced time-dependent inactivation with a K$_i$ of 16.6 μM (Culhane, J. C.; et al. *J Am Chem Soc* 2006, 128 (14), 4536-4537). Propargyl-K4H3$_{1-21}$ was later shown to inactivate LSD1 through formation of a covalent adduct with the enzyme-bound flavin cofactor (Schmidt, D. M.; McCafferty, D. G. *Biochemistry* 2007, 46 (14), 4408-4416; Szewczuk, L. M.; et al. *Biochemistry* 2007, 46, 6892-6902). McCafferty et al. recently described the synthesis of a series of trans-2-arylcyclopropylamine analogues that inhibit LSD1 with $K_i$ values between 188 and 566 (Gooden, D. M.; et al. *Bioorg Med Chem Lett* 2008, 18 (10), 3047-3051). However, in all but one instance, these analogues were 1-2 orders of magnitude more potent against MAO A and MAO B. Most recently, Ueda and coworkers identified small molecule tranylcypromine derivatives that are selective for LSD1 over MAO-A and MAO-B, and Binda et al. described similar tranylcypromine analogues that exhibited partial selectivity between LSD1 and the newly identified histone demethylase LSD2 (Ueda, R.; et al. *J Am Chem Soc* 2009, 131 (48), 17536-17537; Binda, C.; et al. *J Am Chem Soc* 2010, 132, ePub 10.1021/ja101557k).

LSD1 was identified in part because its C-terminal domain shares significant sequence homology with the amine oxidases acetylpolyamine oxidase (APAO) and spermine oxidase (SMO) (Wang, Y.; et al. *Biochem Biophys Res Commun* 2003, 304 (4), 605-611). Several groups have identified amines, guanidines or similar analogues that act as selective modulators of these 2 amine oxidases (Wang, Y.; et al. *Biochem Biophys Res Commun* 2003, 304 (4), 605-611; Ferioli, M. E.; et al. *Toxicol Appl Pharmacol* 2004, 201 (2), 105-111; Casara, P.; et al. *Tet. Letters* 1984, 25, 1891-1894; Bellelli, A.; et al. *Biochem Biophys Res Commun* 2004, 322 (1), 1-8; Wang, Y.; et al. *Cancer Chemother Pharmacol* 2005, 56 (1), 83-90; Cona, A.; et al. *Biochemistry* 2004, 43 (12), 3426-3435; Stranska, J.; et al. *Biochimie* 2007, 89 (1), 135-144). The synthesis of a novel series of (bis)guanidines and (bis)biguanides that are potent antitrypanosomal agents in vitro, with $IC_{50}$ values against *Trypanosoma brucei* as low as 90 nM was also previously reported (Bi, X.; et al. *Bioorg Med Chem Lett* 2006, 16 (12), 3229-3232). We unexpectedly discovered that by further elucidating the structural requirements for binding to LSD1 assisted in identifying potent specific LSD1 inhibitors which are not compounds known to be chemically similar MAO, APAO or SMO inhibitors or derivatives thereof. MAO's are well-known drugs that have been used clinically for the treatment of depression, anxiety, and Parkinson's disease. However if MAO inibitiors are used to inhibit LSD1 to treat disorders such as cancer the risk of unfavourable side effects is likely to increase due to the lack of specificity of the MAO inhibitor. Thus this disclosure presents the first demonstration of small molecule LSD1 inhibitors which are not known to be chemically similar to MAO, APAO or SMO inhibitors or derivatives thereof.

SUMMARY OF THE INVENTION

In one aspect, the invention provides a compound of formula II,

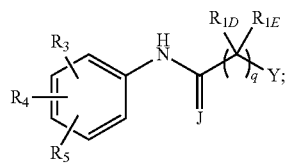

(II)

wherein
Y is (i)

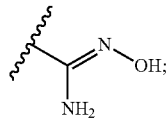

(ii) —C(O)OH; or
(iii) —NH$_2$;

J is O, S, or absent, wherein if J is absent, then the carbon to which J is attached is —CH$_2$—;

$R_3$ is alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

$R_4$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

$R_5$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

wherein $R_3$ is ortho substituted;

each $R_{1D}$ or $R_{1E}$, is independently H, alkyl, aryl, carbocyclic, heterocyclic, alkoxy, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7.

In another aspect, the invention provides a pharmaceutical composition comprising a therapeutically effective amount of a compound of the invention (any of the formulae presented herein), or a pharmaceutically acceptable salt, solvate or hydrate thereof thereof, in combination with a pharmaceutically acceptable carrier or excipient.

In certain aspects, the invention provides a method of treating a disease or disorder associated with lysine-specific demethylase 1 (LSD1) in a subject, the method comprising the step of administering to the subject an effective amount of a compound of the invention (any of the formulae presented herein), or a pharmaceutically acceptable salt, ester or hydrate thereof.

In another aspect, the invention provides a method of treating a disease or disorder associated with lysine-specific demethylase 1 (LSD1) in a subject, wherein the subject is identified as being in need of a LSD1 inhibitor, the method comprising the step of administering to the subject an effective amount of a compound of the invention (any of the formulae presented herein), or a pharmaceutically acceptable salt, ester or hydrate thereof.

In another aspect, the invention provides a method of inhibiting or reducing lysine-specific demethylase 1 (LSD1) in a subject, the method comprising the step of administering to the subject an effective amount of a compound of the invention (any of the formulae presented herein); wherein said compound is identified in a screening assay.

In another aspect, the invention provides a method of treating tumor, cancer, or neoplasia in a subject, the method comprising the step of administering to the subject an effective amount of a compound of the invention (any of the formulae presented herein), or a pharmaceutically acceptable salt, solvate or hydrate thereof.

In another aspect, the invention provides a kit comprising an effective amount of a compound of the invention (any of the formulae presented herein) in unit dosage form, together with instructions for administering the compound to a subject suffering from or susceptible to a LSD1-related disease.

DETAILED DESCRIPTION OF THE INVENTION

Compounds

In one aspect, the invention provides a compound of formula II,

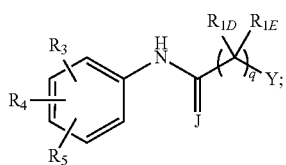
(II)

wherein

Y is (i)

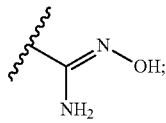

(ii) —C(O)OH; or (iii) —NH$_2$;

J is O, S, or absent, wherein if J is absent, then the carbon to which J is attached is —CH$_2$—;

R$_3$ is alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_4$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_5$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

wherein R$_3$ is ortho substituted;

each R$_{1D}$ or R$_{1E}$, is independently H, alkyl, aryl, carbocyclic, heterocyclic, alkoxy, or halo, each of which is optionally substituted;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7.

In one embodiment, Y is (i)

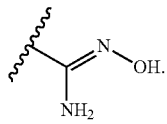

In another embodiment, J is O.

In other embodiments, q is 1.

In certain embodiments, R$_3$ is nitro, hydroxy, thio, C(O)NR$_A$R$_B$, or C(O)OR$_A$.

In a further embodiment, R$_3$ is nitro, hydroxy, thio, C(O)NH$_2$, or C(O)OEt.

In another embodiment, Y is —NH$_2$.

In certain embodiments, J is absent, and the carbon to which J is attached is —CH$_2$—.

In various embodiments, q is 3 or 4.

In still other embodiments, R$_3$ is nitro, hydroxy, thio, C(O)NR$_A$R$_B$, or C(O)OR$_A$.

In other embodiments, R$_4$ is haloalkyl, nitro, hydroxy, thio, C(O)NR$_A$R$_B$, or C(O)OR$_A$.

In another embodiment, R$_5$ is haloalkyl, nitro, hydroxy, thio, C(O)NR$_A$R$_B$, or C(O)OR$_A$.

In certain embodiments, the invention provides a compound of formula II-A,

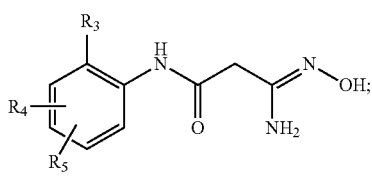
(II-A)

wherein

R$_3$ is nitro, hydroxy, thio, C(O)NR$_A$R$_B$, or C(O)OR$_A$.

R$_4$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_5$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$; and R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

In certain embodiments, $R_3$ is nitro, hydroxy, thio, C(O)NH$_2$, or C(O)OEt, $R_4$ is H and $R_5$ is H.

In other embodiments, the invention provides a compound of formula II-B,

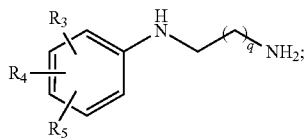
(II-B)

wherein, $R_3$ is nitro, hydroxy, thio, C(O)NR$_A$R$_B$, or C(O)OR$_A$;

$R_4$ is haloalkyl, nitro, hydroxy, thio, C(O)NR$_A$R$_B$, or C(O)OR$_A$;

$R_5$ is haloalkyl, nitro, hydroxy, thio, C(O)NR$_A$R$_B$, or C(O)OR$_A$;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 2 or 3.

In certain embodiments, $R_3$ is nitro, hydroxy, or thio.

In various embodiments, $R_4$ is haloalkyl, nitro, hydroxy, or thio.

In other embodiments, $R_5$ is haloalkyl, nitro, hydroxy, or thio.

Representative novel compounds include, but are not limited to, the following compounds of Table 1:

TABLE 1

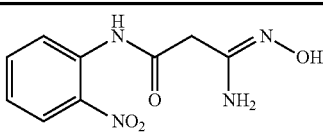

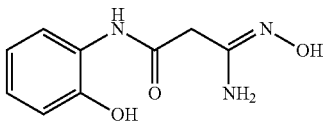

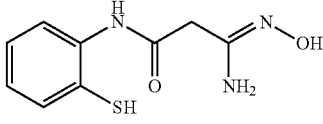

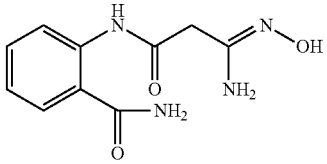 [SMILES: NC(=O)c1ccccc1NC(=O)C/C(N)=N/O]

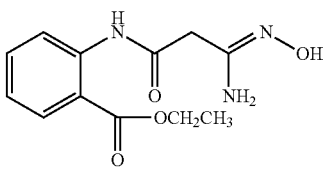 [SMILES: CCOC(=O)c1ccccc1NC(=O)C/C(N)=N/O]

TABLE 1-continued

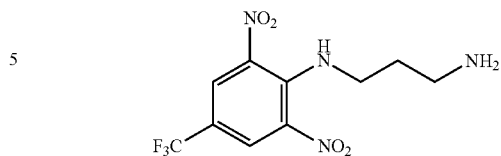

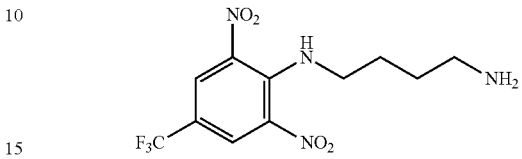

In another aspect, the invention provides a pharmaceutical composition comprising a therapeutically effective amount of a compound of the invention (any of the formulae presented herein), or a pharmaceutically acceptable salt, solvate or hydrate thereof thereof, in combination with a pharmaceutically acceptable carrier or excipient.

In one embodiment, the pharmaceutical composition is in combination with an anti-cancer agent.

Yet another aspect of the present invention is a process of making any of the compounds delineated herein employing any of the synthetic means delineated herein.

Methods of Treatment

In one aspect, the invention provides a method of treating a disease or disorder associated with lysine-specific demethylase 1 (LSD1) in a subject, the method comprising the step of administering to the subject an effective amount of a LSD1 modulator that is not based on a structure of a LSD1 substrate, or a pharmaceutically acceptable salt, ester or hydrate thereof.

In another aspect, the invention provides a method of treating a disease or disorder associated with lysine-specific demethylase 1 (LSD1) in a subject, the method comprising the step of administering to the subject an effective amount of a compound of formula I, formula II, or formula III,

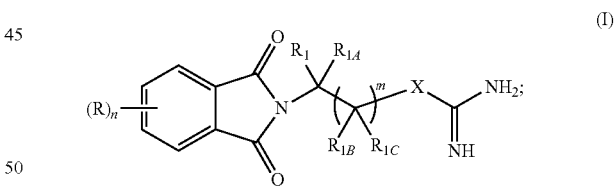
(I)

wherein

X is O, NR$_2$, or S(O)$_p$;

each R is independently selected from optionally substituted alkyl, optionally substituted alkenyl, or optionally substituted alkynyl, each containing 0, 1, 2, or 3 heteroatoms selected from O, S, or N; optionally substituted carbocyclic; optionally substituted heterocyclic; optionally substituted aryl; optionally substituted heteroaryl; halogen, hydroxy, amino, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$;

each R$_1$, R$_{1A}$, R$_{1B}$, or R$_{1C}$, is independently H, alkyl, aryl, carbocyclic, heterocyclic, alkoxy, haloalkyl, or halo, each of which is optionally substituted;

R₂ is optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, 2, 3, or 4;

m is 1, 2, 3, 4, 5, 6, or 7; and p is 0, 1, or 2;

(II)

wherein

Y is (i)

(ii) —C(O)OH; or (iii) —NH₂;

J is O, S, or absent, wherein if J is absent, then the carbon to which J is attached is —CH₂—;

$R_3$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_4$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_5$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

each $R_{1D}$ or $R_{1E}$, is independently H, alkyl, aryl, carbocyclic, heterocyclic, alkoxy, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7; or (III)

wherein

Z is $R_6$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_7$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_8$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

each $R_{1F}$, $R_{1G}$, $R_{1H}$, or $R_{1J}$, is independently H, alkyl, aryl, carbocyclic, heterocyclic, alkoxy, $C(O)OR_A$, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

u is 0, 1, or 2;

r is 1, 2, 3, 4, 5, 6, or 7; and t is 1, 2, 3, 4, 5, 6, or 7;

or a pharmaceutically acceptable salt, ester or hydrate thereof.

In another aspect, the invention provides a method of treating a disease or disorder associated with lysine-specific demethylase 1 (LSD1) in a subject, wherein the subject is identified as being in need of a LSD1 inhibitor, the method comprising the step of administering to the subject an effective amount of a compound of formula I, formula II, or formula III, (I)

[Structure showing phthalimide with R₁, R₁ₐ, R₁ᵦ, R₁c substituents and X, NH₂, NH group, (R)ₙ substituent]

wherein

X is O, $NR_2$, or $S(O)_p$;

each R is independently selected from optionally substituted alkyl, optionally substituted alkenyl, or optionally substituted alkynyl, each containing 0, 1, 2, or 3 heteroatoms selected from O, S, or N; optionally substituted carbocyclic; optionally substituted heterocyclic; optionally substituted aryl; optionally substituted heteroaryl; halogen, hydroxy, amino, —CN, —CF₃, —N₃, —NO₂, —OR_A, —SR_A, —SOR_A, —SO₂R_A, —N(R_A)S(O₂)—R_A, —N(R_A)S(O₂)NR_AR_B, —NR_AR_B, —C(O)OR_A, —C(O)R_A, —C(O)NR_AR_B, or —N(R_A)C(O)R_B;

each $R_1$, $R_{1A}$, $R_{1B}$, or $R_{1C}$, is independently H, alkyl, aryl, carbocyclic, heterocyclic, alkoxy, haloalkyl, or halo, each of which is optionally substituted;

$R_2$ is optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, 2, 3, or 4;

m is 1, 2, 3, 4, 5, 6, or 7; and p is 0, 1, or 2;

(II)

[Structure showing aniline amide with R₃, R₄, R₅ substituents, J, R₁D, R₁E, Y groups]

wherein

Y is (i)

[Structure with N–OH and NH₂ (amidoxime)];

(ii) —C(O)OH; or (iii) —NH₂;

J is O, S, or absent, wherein if J is absent, then the carbon to which J is attached is —CH₂—;

$R_3$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_4$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_5$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

each $R_{1D}$ or $R_{1E}$, is independently H, alkyl, aryl, carbocyclic, heterocyclic, alkoxy, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7; or (III)

[Structure showing diamide with R₆, R₇, R₈ substituents, R₁F, R₁G, R₁H, R₁J groups, and Z]

wherein

Z is

[Structure with NH₂ and C(O)OMe]; [guanidine-type structure with Ph, Ph];

[N-dipropargyl structure]; or [NH-propargyl structure];

$R_6$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_7$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_8$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

each $R_{1F}$, $R_{1G}$, $R_{1H}$, or $R_{1J}$, is independently H, alkyl, aryl, carbocyclic, heterocyclic, alkoxy, $C(O)OR_A$, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

u is 0, 1, or 2;
r is 1, 2, 3, 4, 5, 6, or 7; and
t is 1, 2, 3, 4, 5, 6, or 7, or a pharmaceutically acceptable salt, ester or hydrate thereof.

In certain embodiments, the disease or disorder is selected from: tumor, cancer, blood disorder, neoplasia, skin disorders, neovascularization, inflammatory and arthritic diseases, retinoblastoma, cystoid macular edema (CME), exudative age-related macular degeneration (AMD), diabetic retinopathy, diabetic macular edema, or ocular inflammatory disorders.

In a further embodiment, the disease or disorder is cancer.

In a further embodiment, the disease or disorder is a blood disorder.

In various embodiments, the disease or disorder is hematopoietic cancer, ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain/cns cancer, throat cancer, skin melanoma, acute lymphocytic leukemia, acute myeloid leukemia, cutaneous T-cell lymphoma, mesothelioma, multiple myeloma, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

In certain embodiments, the disease or disorder is myelodysplastic syndrome, refractory anemia, refractory anemia with ringed sideroblasts, refractory anemia with excess blasts, refractory anemia with excess blasts in transformation and refractory cytopenia with multilineage dysplasia.

In another aspect, the invention provides a method of inhibiting or reducing lysine-specific demethylase 1 (LSD1) in a subject, the method comprising the step of administering to the subject an effective amount of a compound of formula I, formula II, or formula III,

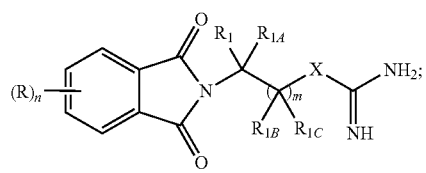

(I)

wherein
X is O, $NR_2$, or $S(O)_p$;
each R is independently selected from optionally substituted alkyl, optionally substituted alkenyl, or optionally substituted alkynyl, each containing 0, 1, 2, or 3 heteroatoms selected from O, S, or N; optionally substituted carbocyclic; optionally substituted heterocyclic; optionally substituted aryl; optionally substituted heteroaryl; halogen, hydroxy, amino, —CN, —$CF_3$, —$N_3$, —$NO_2$, —$OR_A$, —$SR_A$, —$SOR_A$, —$SO_2R_A$, —$N(R_A)S(O_2)$—$R_A$, —$N(R_A)S(O_2)NR_AR_B$, —$NR_AR_B$, —$C(O)OR_A$, —$C(O)R_A$, —$C(O)NR_AR_B$, or —$N(R_A)C(O)R_B$;

each $R_1$, $R_{1A}$, $R_{1B}$, or $R_{1C}$, is independently H, alkyl, aryl, carbocyclic, heterocyclic, alkoxy, haloalkyl, or halo, each of which is optionally substituted;

$R_2$ is optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, 2, 3, or 4;
m is 1, 2, 3, 4, 5, 6, or 7; and
p is 0, 1, or 2;

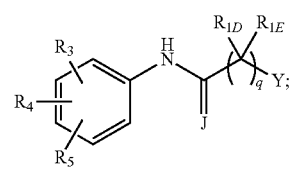

(II)

wherein
Y is (i)

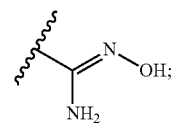

(ii) —C(O)OH; or
(iii) —$NH_2$;

J is O, S, or absent, wherein if J is absent, then the carbon to which J is attached is —$CH_2$—;

$R_3$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_4$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

$R_5$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;

each $R_{1D}$ or $R_{1E}$, is independently H, alkyl, aryl, carbocyclic, heterocyclic, alkoxy, or halo, each of which is optionally substituted;

$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7; or (III)

[Structure diagram showing R₆, R₇, R₈ substituted phenyl connected via NH-C(O)-(CR₁FR₁G)r-C(O)-NH-(CR₁HR₁J)t-Z]

wherein

Z is

[Structures showing: -C(NH₂)C(O)OMe; -NH-C(=A)-NH-CH₂-CH(Ph)(Ph) with subscript u; -N(CH₂C≡CH)₂; or -CH(CH₂C≡CH)NH-]

R₆ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R₇ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R₈ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

each R$_{1F}$, R$_{1G}$, R$_{1H}$, or R$_{1J}$, is independently H, alkyl, aryl, carbocyclic, heterocyclic, alkoxy, C(O)OR$_A$, or halo, each of which is optionally substituted;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

u is 0, 1, or 2;

r is 1, 2, 3, 4, 5, 6, or 7; and t is 1, 2, 3, 4, 5, 6, or 7;

wherein said compound is identified in a screening assay.

In certain embodiments, the screening assay is a demethylase assay.

In a further embodiment, the LSD1 inhibitor has a IC$_{50}$ for inhibiting LSD1 less than about 5 micromolar.

In another aspect, the invention provides a method of treating tumor, cancer, blood disorder or neoplasia in a subject, the method comprising the step of administering to the subject an effective amount of a compound of formula I, formula II, or formula III, (I)

[Structure diagram of phthalimide with (R)$_n$ substituents, connected via N-CR₁R$_{1A}$-(CR$_{1B}$R$_{1C}$)$_m$-X-C(=NH)NH₂]

wherein

X is O, NR₂, or S(O)$_p$;

each R is independently selected from optionally substituted alkyl, optionally substituted alkenyl, or optionally substituted alkynyl, each containing 0, 1, 2, or 3 heteroatoms selected from O, S, or N; optionally substituted carbocyclic; optionally substituted heterocyclic; optionally substituted aryl; optionally substituted heteroaryl; halogen, hydroxy, amino, —CN, —CF₃, —N₃, —NO₂, —OR$_A$, —SR$_A$, —SOR$_A$, —SO₂R$_A$, —N(R$_A$)S(O₂)—R$_A$, —N(R$_A$)S(O₂)NR$_A$R$_B$, —NR$_A$R$_B$, —C(O)OR$_A$, —C(O)R$_A$, —C(O)NR$_A$R$_B$, or —N(R$_A$)C(O)R$_B$;

each R₁, R$_{1A}$, R$_{1B}$, or R$_{1C}$, is independently H, alkyl, aryl, carbocyclic, heterocyclic, alkoxy, haloalkyl, or halo, each of which is optionally substituted;

R₂ is optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, 2, 3, or 4;

m is 1, 2, 3, 4, 5, 6, or 7; and p is 0, 1, or 2;

(II)

[Structure diagram showing R₃, R₄, R₅ substituted phenyl-NH-C(=J)-(CR$_{1D}$R$_{1E}$)$_q$-Y]

wherein

Y is (i)

[Structure: -C(=N-OH)NH₂]

(ii) —C(O)OH; or (iii) —NH₂;

J is O, S, or absent, wherein if J is absent, then the carbon to which J is attached is —CH₂—;

R₃ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_4$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_5$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

each R$_{1D}$ or R$_{1E}$, is independently H, alkyl, aryl, carbocyclic, heterocyclic, alkoxy, or halo, each of which is optionally substituted;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7; or

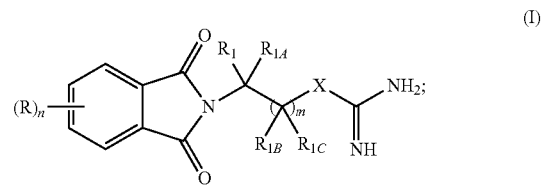

wherein
Z is

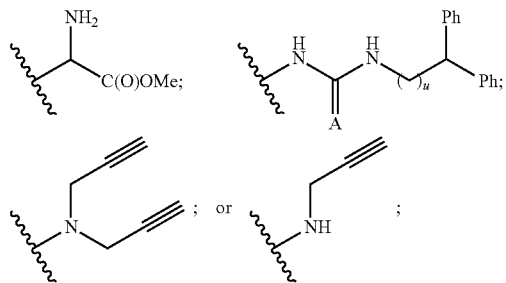

R$_6$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_7$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_8$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

each R$_{1F}$, R$_{1G}$, R$_{1H}$, or R$_{1J}$, is independently H, alkyl, aryl, carbocyclic, heterocyclic, alkoxy, C(O)OR$_A$, or halo, each of which is optionally substituted;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

u is 0, 1, or 2;
r is 1, 2, 3, 4, 5, 6, or 7; and
t is 1, 2, 3, 4, 5, 6, or 7;
or a pharmaceutically acceptable salt, solvate or hydrate thereof.

In certain embodiments, the compound inhibits LSD1 to thereby treat the tumor, cancer, blood disorder or neoplasia.

In various embodiments, the invention provides a method described above wherein the compound is formula I:

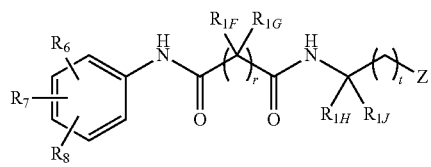

wherein
X is S;
each R is independently selected from optionally substituted alkyl, optionally substituted alkenyl, or optionally substituted alkynyl, each containing 0, 1, 2, or 3 heteroatoms selected from O, S, or N; optionally substituted carbocyclic; optionally substituted heterocyclic; optionally substituted aryl; optionally substituted heteroaryl; halogen, hydroxy, amino, —CN, —CF$_3$, —N$_3$, —NO$_2$, —OR$_A$, —SR$_A$, —SOR$_A$, —SO$_2$R$_A$, —N(R$_A$)S(O$_2$)—R$_A$, —N(R$_A$)S(O$_2$)NR$_A$R$_B$, —NR$_A$R$_B$, —C(O)OR$_A$, —C(O)R$_A$, —C(O)NR$_A$R$_B$, or —N(R$_A$)C(O)R$_B$;

each of R$_1$, R$_{1A}$, R$_{1B}$, and R$_{1C}$, is H;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

n is 0, 1, 2, 3, or 4; and
m is 1, 2, 3, 4, 5, 6, or 7.
In certain embodiments, n is 0.
In other embodiments, m is 1, 2, or 3.
In various embodiments, the invention provides a method described above wherein the compound is formula II:

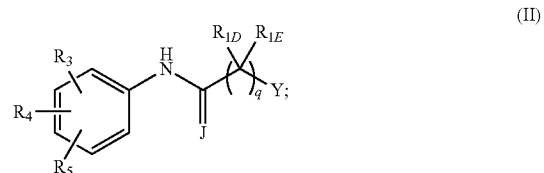

wherein
Y is (i)

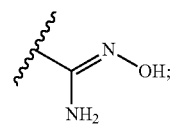 [SMILES: */C(N)=N/O]

(ii) —C(O)OH; or
(iii) —NH$_2$;

J is O or absent, wherein if J is absent, the carbon to which J is attached is —CH$_2$—;

R$_3$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_4$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_5$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

each R$_{1D}$ or R$_{1E}$, is H;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and q is 1, 2, 3, 4, 5, 6, or 7.

In certain embodiments, Y is

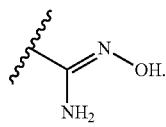

In other embodiments, J is O.

In various embodiments, R$_3$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In certain embodiments, R$_4$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In other embodiments, R$_5$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In still other embodiments, Y is —NH$_2$.

In various embodiments, J is absent, wherein if J is absent, the carbon to which J is attached is —CH$_2$—.

In another embodiment, R$_3$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In other embodiments, R$_4$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In other embodiments, R$_5$ is H, Me, Et, i-Pr, methoxy, ethoxy, phenoxy, F, Cl, Br, phenyl, CF$_3$, nitro, hydroxy, thio, C(O)NH$_2$, or C(O)OEt.

In certain embodiments, Y is —C(O)OH.

In various embodiments, J is O.

In certain embodiments, R$_3$ is H, Me, Et, i-Pr, methoxy, ethoxy, phenoxy, F, Cl, Br, phenyl, CF$_3$, nitro, hydroxy, or thio.

In various embodiments, R$_4$ is H, Me, Et, i-Pr, methoxy, ethoxy, phenoxy, F, Cl, Br, phenyl, CF$_3$, nitro, hydroxy, or thio.

In still other embodiments, R$_5$ is H, Me, Et, i-Pr, methoxy, ethoxy, phenoxy, F, Cl, Br, phenyl, CF$_3$, nitro, hydroxy, or thio.

In various embodiments, the invention provides a method described above wherein the compound is formula III:

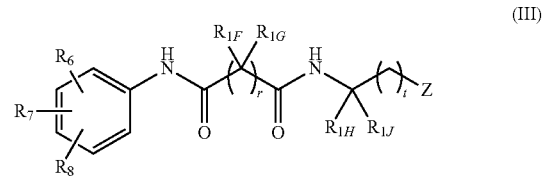

(III)

wherein
Z is

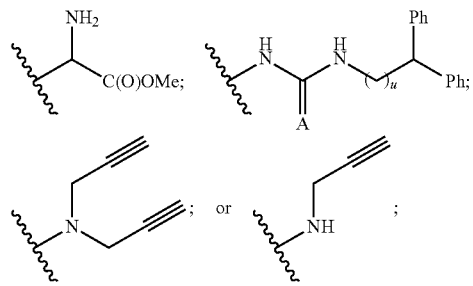

R$_6$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_7$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

R$_8$ is H, alkyl, aryl, carbocyclic, heterocyclic, aralkyl, alkoxy, aryloxy, haloalkyl, or halo, each of which is optionally substituted, nitro, hydroxy, thio, C(O)NR$_A$R$_B$, or C(O)OR$_A$;

each R$_{1F}$ or R$_{1G}$ is H;

each R$_{1H}$ or R$_{1J}$ is independently H or C(O)OR$_A$;

R$_A$ and R$_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen;

u is 0, 1, or 2;

r is 1, 2, 3, 4, 5, 6, or 7; and t is 1, 2, 3, 4, 5, 6, or 7.

In certain embodiments, R$_6$ is H or halo; R$_7$ is H or halo; and R$_8$ is H or halo.

In various embodiments, the invention provides a method described above further comprising an additional therapeutic agent.

In certain embodiments, the additional therapeutic agent is a LSD1 inhibiting compound.

In another embodiment, the additional therapeutic agent is an anticancer compound.

In various embodiments, the invention provides a method described above wherein the step of administering the compound comprises administering the compound orally, topically, parentally, intravenously or intramuscularly.

In various embodiments, the invention provides a method described above wherein the subject is a human.

In certain embodiments, the invention provides a compound, composition, kit, or method of treatment as described herein, wherein the compound of the invention is selected from any of the formulae as described here, or is selected from a compound in Table 1 or Table 2.

In certain embodiments, the invention provides a method wherein the disease or disorder associated with LSD1 is a skin disorder.

In a further embodiment, the disease or disorder is psoriasis, acne, rosacea, warts, eczema, hemangiomas, lymphangiogenesis, Sturge-Weber syndrome, venous ulcers of the skin, neurofibromatosis, and tuberous sclerosis.

In another embodiment, the invention provides a method wherein the disease or disorder associated with LSD1 is neovascularization.

In a further embodiment, the disease or disorder is malaria, diabetic retinopathy, retinopathy of prematurity, corneal graft rejection, neovascular glaucoma, retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications, and diseases associated with rubeosis (neovascularization of the ankle).

In other embodiments, the invention provides a method wherein the disease or disorder associated with LSD1 is inflammatory and arthritic disease.

In a further embodiment, the disease or disorder is: rheumatoid arthritis, osteoarthritis, lupus, scleroderma, Crohn's disease, ulcerative colitis, psoriasis, sarcoidosis, Sarcoidosis, skin lesions, hemangiomas, Osler-Weber-Rendu disease, hereditary hemorrhagic telangiectasia, and osteoarthritis.

In another embodiment, the invention provides a method wherein the disease or disorder affects the dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

The term "inhibitory amount" of a compound of the present invention means a sufficient amount to decrease the disorder/cancer in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin, which may be intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof; or stem cells.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily inhibitory dose of the compounds of this invention administered to a subject in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In one embodiment, treatment regimens according to the present invention comprise administration to a patient in need of such treatment from about 10 mg to about 1000 mg of the compound(s) of this invention per day in single or multiple doses. In another embodiment, the treatment regimen comprises administration to a patient in need of such treatment from about 25 mg to about 6000 mg of a compound(s) of this invention per day in single or multiple doses. For instance a compound of the present invention can be administered to a patient twice a day with a total daily dose of 4000, 4200, 4400, 4600, 4800 or 5000 mg.

Biological Data

LSDI is a Validated Target for Cancer Chemotherapy.

Recent studies suggest that LSD1 hyperactivity plays an important role in the development of cancer. LSD1 is frequently part of larger transcriptional repressor complexes that are associated with aberrant gene silencing. These transcriptional repressor complexes often include histone deacetlyases, DNA methyltransferase, polycomb repressor proteins, and other proteins known to inhibit transcription and mark chromatin for silencing. It has also been suggested that LSD1 is a prognostic marker for aggressive breast cancer. (Lim, S. Et al., *Carcinogenesis*. 2010; March; 31(3): 512-20).

High levels of LSD1, nuclear expression of the FHL2 co-activator, high Gleason score and grade, and very strong staining of nuclear p53 correlate significantly with relapse of prostate carcinoma during follow-up. Thus LSD1 and nuclear FHL2 may serve as novel biomarkers predictive for prostate cancer with aggressive biology and point to a role of LSD1 and FHL2 in constitutive activation of AR-mediated growth signals. In neuroblastoma, small interfering RNA—mediated knockdown of LSD1 decreased cellular growth, induced expression of differentiation-associated genes, and increased target gene—specific H3K4 methylation.

LSDI inhibition using monoamine oxidase inhibitors resulted in an increase of global H3K4 methylation and growth inhibition of neuroblastoma cells in vitro, and reduced neuroblastoma xenograft growth in vivo. Thus, LSD1 is involved in maintaining the undifferentiated, malignant phenotype of neuroblastoma cells, and inhibition of LSD1 reprograms the transcriptome of neuroblastoma cells and inhibits neuroblastoma xenograft growth. Recent studies in our laboratories also suggest that LSD1 inhibitors can be effective as antitumor agents in vivo. Previously, various polyaminobiguanidides were evaluated in an HCT116 human colon tumor xenograft model in athymic nu/nu Fox Chase mice. Mice were treated with polyaminobiguanidides, 5-azacytidine (5-AC) or a combination of the two agents. Drugs were administered 5 times a week over a period of 38 days. Polyaminobiguanidides alone was no more effective than vehicle at a dose of 10 mg/kg, while 5-AC at 2 mg/kg reduced tumor growth by about 50%. However, the combination of 10 mg/kg polyaminobiguanidides plus 1 mg/kg 5-AC was very effective at limiting tumor growth, and was significantly more effective than 5-AC alone. It should also be noted that the inhibition of tumor growth was accompanied by a global increase of tumor dimethyl lysine 4 of histone 3 indicating functional inhibition of LSD1 in vivo. The studies outlined above strongly support the contention that LSD1 inhibitors that promote re-expression of aberrantly silenced tumor suppressor genes can be of benefit when used alone or in combination with established antitumor agents.

Inhibitors from the Maybridge Database.

The Maybridge Hitfinder 5 Library was examined using a virtual screen to identify lead compounds for the discovery of new LSD1 inhibitors. The crystal structure of LSD1 (Protein Database #2v1d) was prepared for virtual screening and used to assess the "drugability" of the LSD1 histone binding pocket, and to map the active site. Two dimensional representations of the compounds in the Maybridge database were converted to 3D, and conformational analysis performed to determine appropriate candidates for docking in the LSD1 active site. The best 10 hits were examined and of these two seemed amenable to structural modification were selected. These are shown in Scheme A.

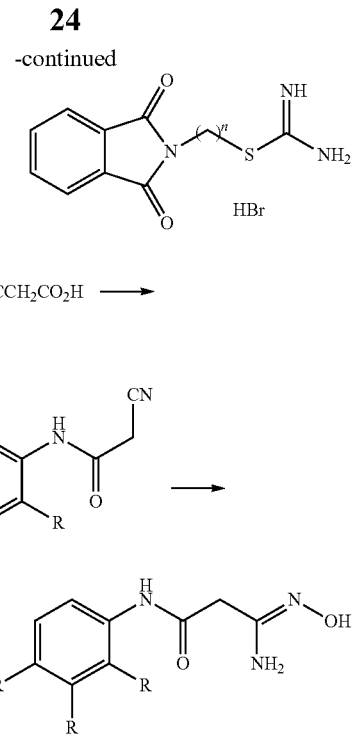

A library of homologues, as shown in Scheme A was subsequently synthesized. Thus, the commercially available bromothalimides were refluxed in ethanol in the presence of thiourea to afford the desired analogues. Likewise, an appropriate aryl amine was added to 2-cyanoacetic acid (PCl$_5$) to yield the intermediate cyano compounds. Reaction of these species with hydroxylamine then afforded the desired target compounds.

The other compounds of the invention can be synthesized according to the following synthetic schemes below.

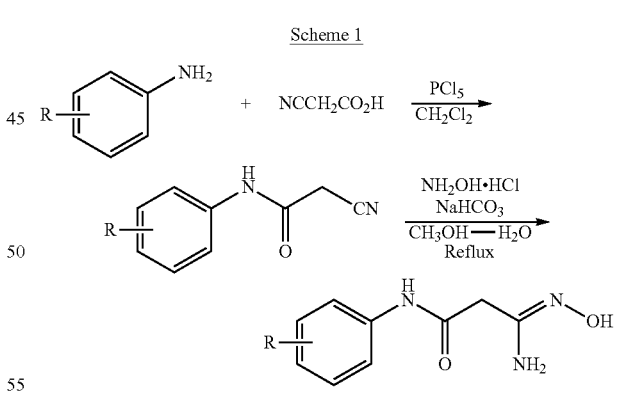

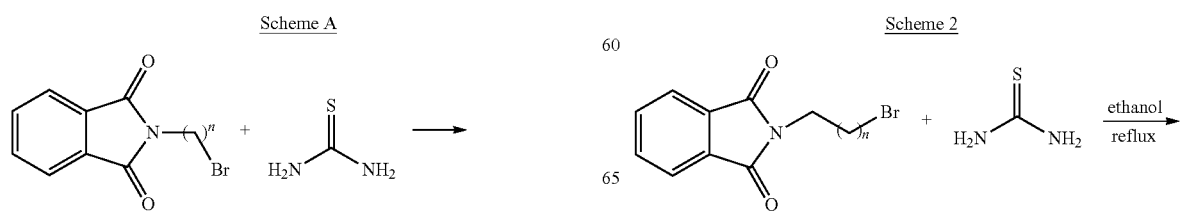

-continued

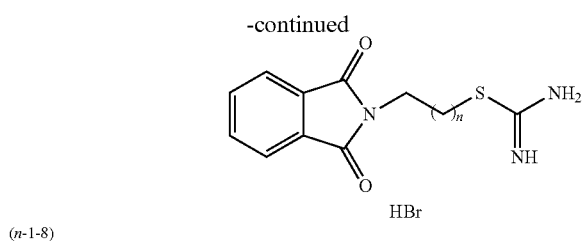

(n-1-8)

Scheme 3

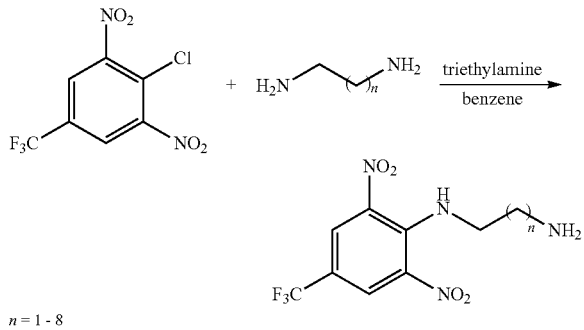

n = 1 - 8

DEFINITIONS

Listed below are definitions of various terms used to describe this invention. These definitions apply to the terms as they are used throughout this specification and claims, unless otherwise limited in specific instances, either individually or as part of a larger group. The number of carbon atoms in a hydrocarbyl substituent can be indicated by the prefix "$C_x$-$C_y$," where x is the minimum and y is the maximum number of carbon atoms in the substituent. Likewise, a $C_x$ chain means a hydrocarbyl chain containing x carbon atoms.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein at least one hydrogen radical is replaced with a halogen radical.

If a linking element in a depicted structure is "absent" or "a bond", then the left element in the depicted structure is directly linked to the right element in the depicted structure. For example, if a chemical structure is depicted as X-(L)$_n$-Y wherein L is absent or n is 0, then the chemical structure is X—Y.

The term "alkyl" as used herein, refers to a saturated, straight- or branched-chain hydrocarbon radical. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds. For example, "$C_2$-$C_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds. For example, "$C_2$-$C_8$ alkynyl" contains from from two to eight carbon atoms. Representative alkynyl groups include, but are not limited to, for example, ethynyl, 1-propynyl, 1-butynyl, heptynyl, octynyl and the like.

The term "cycloalkyl" denotes a monovalent group derived from a monocyclic or polycyclic saturated carbocyclic ring compound. Examples of cycloalkyl include, but not limited to, cyclopropyl, cyclobutyl, cyclopentyl, cyclohexyl, bicyclo[2.2.1]heptyl, and bicyclo[2.2.2]octyl and the like. The terms "carbocycle" or "carbocyclic" or "carbocyclyl" refer to a saturated (e.g., "cycloalkyl"), partially saturated (e.g., "cycloalkenyl" or "cycloalkynyl") or completely unsaturated (e.g., "aryl") ring system containing zero heteroatom ring atom. A carbocyclyl may be, without limitation, a single ring, or two or more fused rings, or bridged or spiro rings. A carbocyclyl may contain, for example, from 3 to 10 ring members (i.e., $C_3$-$C_{10}$carbocyclyl, such as $C_3$-$C_{10}$cycloalkyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl and the like. A carbocyclyl group can be attached to the parent molecular moiety through any substitutable carbon atom of the group.

The term "aryl" refers to an aromatic carbocyclyl containing from 6 to 14 carbon ring atoms. Non-limiting examples of aryls include phenyl, naphthalenyl, anthracenyl, and indenyl and the like. An aryl group can be connected to the parent molecular moiety through any substitutable carbon atom of the group.

The term "heteroaryl" means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heterocycloalkyl" refers to a non-aromatic 3-, 4-, 5-, 6- or 7-membered ring or a bi- or tri-cyclic group fused system, where at least one of the ring atoms is a heteroatom, and where (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl and the like.

The terms "heterocyclic" or "heterocycle" or "heterocyclyl" refer to a saturated (e.g., "heterocycloalkyl"), partially unsaturated (e.g., "heterocycloalkenyl" or "heterocycloalkynyl") or completely unsaturated (e.g., "heteroaryl") ring system, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results. A heterocyclyl may be, without limitation, a single ring. Non-limiting examples of single-ring heterocyclyls include furanyl, dihydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazoly, pyranyl, dihydropyranyl, pyridinyl, piperidinyl, pyridazinyl, pyrimidinyl, pyrazinyl, piperazinyl, triazinyl, isoxazinyl, oxazolidinyl, isoxazolidinyl, oxathiazinyl, oxadiazinyl, morpholinyl, azepinyl, oxepinyl, thiepinyl, or diazepinyl. A heterocyclyl may also include, without limitation, two or more rings fused together, such as, for example, naphthyridinyl, thiazolpyrimidinyl, thienopyrimidinyl, pyrimidopyrimidinyl, or pyridopyrimidinyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

The terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

-alkyl, -alkenyl, -alkynyl, -aryl, -arylalkyl, -heteroaryl, -heteroarylalkyl, -heterocycloalkyl, -cycloalkyl, -carbocyclic, -heterocyclic, —F, —Cl, —Br, —I, —OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O-alkyl, —O-alkenyl, —O-alkynyl, —O-cycloalkyl, —O-aryl, —O-heteroaryl, —O-heterocyclic, —C(O)-alkyl, —C(O)-alkenyl, —C(O)-alkynyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-alkynyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-alkynyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-alkynyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-alkynyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-alkynyl, —$NHCO_2$-cycloalkyl, —$NHCO_2$-aryl, —$NHCO_2$-heteroaryl, —$NHCO_2$-heterocycloalkyl, —NHC(O)$NH_2$, —NHC(O)NH-alkyl, —NHC(O)NH-alkenyl, —NHC(O)NH-alkenyl, —NHC(O)NH-cycloalkyl, —NHC(O)NH-aryl, —NHC(O)NH-heteroaryl, —NHC(O)NH-heterocycloalkyl, NHC(S)$NH_2$, —NHC(S)NH-alkyl, —NHC(S)NH-alkenyl, —NHC(S)NH-alkynyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHC(NH)-alkyl, —NHC(NH)-alkenyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-alkynyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-alkynyl, —S(O)-cycloalkyl, —S(O)-aryl, —S(O)-heteroaryl, —S(O)-heterocycloalkyl-$SO_2NH_2$, —$SO_2$NH-alkyl, —$SO_2$NH-alkenyl, —$SO_2$NH-alkynyl, —$SO_2$NH-cycloalkyl, —$SO_2$NH-aryl, —$SO_2$NH-heteroaryl, —$SO_2$NH-heterocycloalkyl, —$NHSO_2$-alkyl, —$NHSO_2$-alkenyl, —$NHSO_2$-alkynyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, polyalkoxyalkyl, polyalkoxy, -methoxymethoxy, -methoxyethoxy, —SH, —S-alkyl, —S-alkenyl, —S-alkynyl, —S-cycloalkyl, —S-aryl, —S-heteroaryl, —S-heterocycloalkyl, or methylthiomethyl.

It is understood that the aryls, heteroaryls, carbocycles, heterocycles, alkyls, and the like can be further substituted.

The terms "halo" and "halogen," as used herein, refer to an atom selected from fluorine, chlorine, bromine and iodine.

The term "subject" as used herein refers to a mammal. A subject therefore refers to, for example, dogs, cats, horses, cows, pigs, guinea pigs, and the like. Preferably the subject is a human. When the subject is a human, the subject may be either a patient or a healthy human.

The term "leaving group," or "LG", as used herein, refers to any group that leaves in the course of a chemical reaction involving the group and includes but is not limited to halogen, brosylate, mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, Protective Groups in Organic Synthesis, 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl(trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, Protective Groups in Organic Synthesis, 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino," as used herein, refers to an amino group protected with an amino protecting group as defined above.

The term "alkylamino" refers to a group having the structure —N(R$_a$R$_b$), where R$_a$ and R$_b$ are independent H or alkyl.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, or magnesium salts, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This invention also encompasses pharmaceutical compositions containing pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

As used herein, "solvate" refers to the physical association of a compound of the invention with one or more solvent molecule, whether organic or inorganic. This physical association often includes hydrogen bonding. In certain instances, the solvate is capable of isolation, for example, when one or more solvate molecules are incorporated in the crystal lattice of the crystalline solid.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups, and elixirs. In addition to the active compounds, the liquid dosage forms may contain inert diluents commonly used in the art such as, for example, water, alcohol or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, polysorbate, dimethylformamide, oils (in particular, cottonseed, groundnut, corn, germ, olive, castor, and sesame oils), mono- or diglycerides, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, antioxidants, sweetening, flavoring, and perfuming agents. The liquid dosage form can also be encapsulated in a gelatin capsule, wherein a compound of the present invention can be dissolved in a pharmaceutically acceptable carrier containing, for example, one or more solubilizing agents (e.g., polysorbate 80 and mono and diglycerides), and other suitable excipients (e.g., an antioxidants such as ascorbyl palmitate, or a sweetening or flavoring agent).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Immediate release forms are also contemplated by the present invention.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above.

The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Preferably, a compound of the invention is formulated in a solid dispersion, where the compound can be molecularly dispersed in a matrix which comprises a pharmaceutically acceptable, hydrophilic polymer. The matrix may also contain a pharmaceutically acceptable surfactant. Suitable solid dispersion technology for formulating a compound of the invention includes, but is not limited to, melt extrusion, spray drying, or solvent evaporation.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, cancer is treated in a subject, such as a human or another animal, by administering to the subject a therapeutically effective amount of a compound of the invention (or a pharmaceutically acceptable salt, ester or prodrug thereof), in such amounts and for such time as is necessary to achieve the desired result. The term "therapeutically effective amount" of a compound of the invention, as used herein, means a sufficient amount of the compound so as to decrease the subject's symptoms. As is well understood in the medical arts a therapeutically effective amount of a compound of this invention will be at a reasonable benefit/risk ratio applicable to any medical treatment.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

EXAMPLES

The compounds and processes of the present invention will be better understood in connection with the following examples, which are intended as an illustration only and not to limit the scope of the invention. The following examples can be prepared according to the schemes as described above, or according to the synthetic steps as described below. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The chemical structures herein contain certain —NH—, —NH$_2$ (amino) and —OH (hydroxyl) groups where the corresponding hydrogen atom(s) may not explicitly appear; however they are to be read as —NH—, —NH$_2$ or —OH as the case may be.

All reagents and dry solvents were purchased from Aldrich Chemical Co. (Milwaukee, Wis.), Sigma Chemical Co. (St. Louis, Mo.) or Acros Chemical (Chicago, Ill.) and were used without further purification except as noted below. Pyridine was dried by passing it through an aluminum oxide column and then stored over KOH. Triethylamine was distilled from potassium hydroxide and stored in a nitrogen atmosphere. Methanol was distilled from magnesium and iodine under a nitrogen atmosphere and stored over molecular sieves. Methylene chloride was distilled from phosphorus pentoxide and chloroform was distilled from calcium sulfate. Tetrahydrofuran was purified by distillation from sodium and benzophenone. Dimethyl formamide was dried by distillation from anhydrous calcium sulfate and was stored under nitrogen. Preparative scale chromatographic procedures were carried out using E. Merck silica gel 60, 230-440 mesh. Thin layer chromatography was conducted on Merck precoated silica gel 60 F-254. Ion exchange chromatography was conducted on Dowex 1X8-200 anion exchange resin. The syntheses of any starting materials/intermediates not specifically delineated herein were performed according to literature precedent.

All $^1$H- and $^{13}$C-NMR spectra were recorded on a Varian Mercury 400 mHz spectrometer, and all chemical shifts are reported as δ values referenced to TMS or DSS. Infrared spectra were recorded on a Jasco FT-IR spectrophotometer and are referenced to polystyrene. In all cases, $^1$H-NMR, $^{13}$C-NMR and IR spectra were consistent with assigned structures. Mass spectra were recorded on a Kratos MS 80 RFA (EI and CI) or Kratos MS 50 TC (FAB) mass spectrometer. Prior to biological testing, any compounds described by this invention were determined to be 95% pure or greater by HPLC chromatography using an Agilent Series 1100 high-performance liquid chromatograph fitted with a C18 reversed-phase column.

Synthetic H3K4me2 peptides were purchased from Millipore (Billerica, Mass.). Calu-6 cells were maintained in RPMI medium, both supplemented with 10% fetal bovine serum (Gemini Bio-Products, Woodland, Calif.) and grown at 37° C. in 5% $CO_2$ atmosphere.

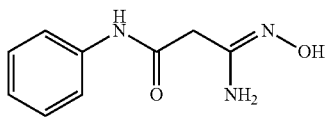 [SMILES: N/C(CC(=O)Nc1ccccc1)=N\O]

Example 1

Synthesis of

Scheme 1

Cyanoacetic acid (0.96 g, 11.1 mmol, 1 eq) was added to a mixture of $PCl_5$ (2.35 g, 11.1 mmol, 1 eq) in 200 mL of $CH_2Cl_2$, and the mixture refluxed for 30 minutes. After cooling, aniline (1.01 mL, 1.03 g, 11.1 mmol) was added and the solution was refluxed for 2 hrs. The reaction mixture was allowed to cool to room temperature, and then concentrated to dryness at the rotary evaporator. A 50 mL portion of water was added and the suspension was filtered. The resulting solid was then washed with 25 mL of 1.0 N $NaHCO_3$ solution, 25 mL of water and then dried to afford the desired cyanoamide as a white amorphous solid (1.64 g, 92%). This solid was of sufficient purity to be used without further purification in the subsequent reaction. $^1$H NMR (400 MHz, acetone-d$_6$) δ 9.58 (s, 1H), 7.62 (d, J=8.4 Hz, 2H), 7.33 (t, J=8.0 Hz, 2H), 7.11 (t, J=7.2 Hz, 1H), 3.82 (s, 2H).

A 0.9 g portion (12.8 mmol, 1.25 eq) of $NH_2OH \cdot HCl$ was added to $Na_2CO_3$ (1.36 g, 12.8 mmol, 1.25 eq) dissolved in 5 mL of water, and the solution was diluted with 50 mL of methanol. The cyanoamide from the previous step (1.64 g, 10.2 mmol) was added and the mixture was refluxed for 2 hours. After cooling, the reaction mixture was concentrated in vacuo, and the resulting solid was mixed with a hot 3:1 mixture of ethyl acetate:hexane. The insoluble material was immediately removed by filtration, and the filtrate was concentrated to dryness at the rotary evaporator. The solid residue was purified by column chromatography (silica gel, ethyl acetate:methanol 20:1) and recrystallized to afford Example 1 as a white crystalline solid (0.67 g, 34%). $^1$H NMR (400 MHz, acetone-d$_6$) δ 9.53 (s, 1H), 8.70 (s, 1H), 7.65-7.63 (m, 2H), 7.31-7.27 (m, 2H), 7.07-7.04 (m, 1H), 5.39 (s, 2H), 3.17 (s, 2H).

Example 2

Synthesis of

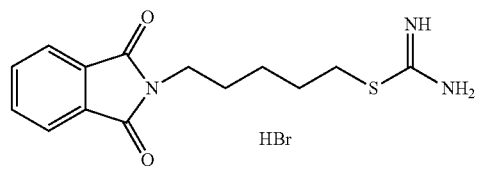 [SMILES: N=C(N)SCCCCCN1C(=O)c2ccccc2C1=O ; Br]

Scheme 2

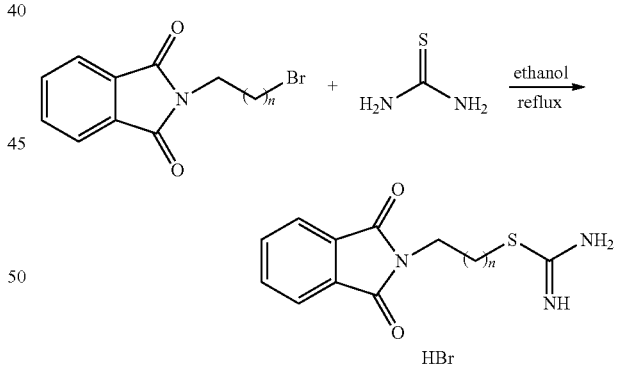

A mixture of 5.0 g (16.8 mmol) of N-(5-bromopentyl) phthalimide (n=4) and 1.41 g (18.5 mmol) of thiourea was heated at reflux in 10 ml of absolute ethanol (EtOH) for 18 h. The mixture was cooled to room temperature, and the product was collected by filtration and then washed with two 10-ml portions of chilled EtOH and four 15-ml portions of acetone and dried under vacuum. The product was obtained as a colorless solid: yield 5.62 g (90%); mp 188 to 190° C. $^1$H NMR (400 mHz, DMSO-d$_6$) δ 1.42 (m, 2H), 1.65 (m, 4H), 3.15 (t, 2H, J 7.2 Hz), 3.61 (t, 2H, J 6.9 Hz), 7.90 (m, 4H), and 8.97 (br s, 4H).

Example 3

Synthesis of

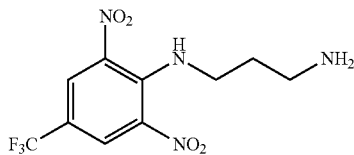

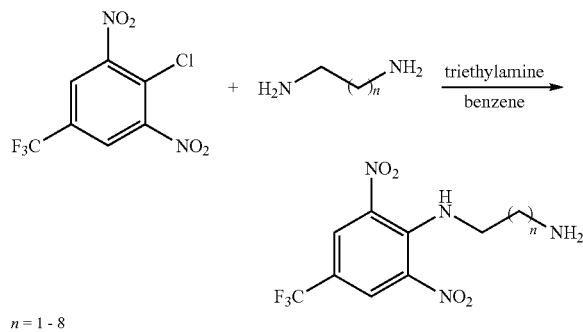

$n = 1-8$

A solution of 1,3-diaminopropane (7.49 mL, 6.67 g, 100 mmol, 20 eq) and triethylamine (0.70 mL, 0.51 g, 5.0 mmol, 1 eq) in 40 mL of benzene was cooled to 10° C., and a 4-chloro-3,5-dinitrobenzotrifluoride in 40 mL of benzene was added dropwise over a period of 2 hours. The reaction was warmed to room temperature and allowed to stir overnight, after which it was concentrated in vacuo to yield an orange liquid. This residue was dissolved in 200 mL of ethyl acetate and the organic layer was washed with 2 25 mL portions of water and 25 mL of saturated aqueous NaCl. The ethyl acetate layer was dried over anhydrous $MgSO_4$ and concentrated, and the crude mixture was purified by column chromatography using a solvent gradient (1:1 hexanes:ethyl acetate to ethyl acetate to 3:1 ethyl acetate:methanol). The desired fractions were pooled and concentrated to give an orange solid, which was dissolved in ethyl acetate. 1.0 M HCl in ethyl acetate was added slowly until no more product precipitated from the solution. The solid product was collected by filtration and washed with 25 mL of ethyl acetate to afford pure ASH-83-45 free base as a yellow solid (1.30 g, 87%). $^1$H NMR (400 MHz, $CDCl_3$) δ 9.52 (bs, 1H), 8.39 (s, 2H), 3.14 (s, 2H), 2.94 (t, J=6.0 Hz, 2H), 1.78 (p, J=6.0 Hz, 2H), 1.33 (bs, 2H). $^{19}$F NMR (376 MHz, $CDCl_3$) δ −62.36 (s, 3F).

Example 4

Expression, Purification and Demethylase Assay of Recombinant Proteins

Full-length human LSD1 cDNA was subcloned into the pET15b bacterial expression vector (Novagen, Madison, Wis.) in frame with an N-terminal 6xHIS-tag and transformed into the $BL_{21}(DE_3)$ strain of *Escherichia coli*. Following selection, expression and purification of recombinant LSD1 protein were performed as previously described. Briefly, expression of LSD1-HIS protein was induced by 1 mM IPTG for 6 h at 25° C. The HIS-tagged protein was purified using Ni-NTA affinity purification resin and column as recommended by the manufacturer (Qiagen, Valencia, Calif.). Bound protein was eluted by imidazole and the eluate was dialyzed in PBS at 4° C. Enzymatic activity of LSD1 was examined using luminol-dependent chemiluminescence to measure the production of $H_2O_2$, as previously described. In brief, LSD1 activity was assayed in 50 mM Tris, pH 8.5, 50 mM KCl, 5 mM MgCl, 5 nmol luminol, and 20 μg/ml horseradish peroxidase with the indicated concentrations of H3K4me2 (1-21 aa) peptide as substrate. The integral values were calibrated against standards containing known concentrations of $H_2O_2$, and the activities expressed as pmols $H_2O_2$/mg protein/min. Reaction mixtures were incubated with or without 5 μg purified LSD1 in 50 mM Tris, pH 8.5, 50 mM KCl, 5 mM MgCl, 0.5% BSA, and 5% glycerol for 3 hr at 37° C. This reaction mixture was analyzed by Western blotting using antibodies (Millipore) that specifically recognize the dimethyl group of H3K4.

Western Blotting.

Cytoplasmic and nuclear fractions were prepared for Western blot analysis using the NE-PER™ Nuclear and Cytoplasmic Extraction Kit (Pierce, Rockford, Ill.). Primary antibodies against H3K4me2 were from Millipore. The pCNA monoclonal antibody was purchased from Oncogene Research Products (Cambridge, Mass.). Dye-conjugated secondary antibodies were used for quantification of Western blot results using the Odyssey Infrared Detection system and software (LI-COR Biosciences, Lincoln, Nebr.).

RNA Isolation and qPCR.

RNA was extracted using TRIzol reagents (Invitrogen, Carlsbad, Calif.). First-strand cDNA was synthesized using SuperScript III reverse transcriptase with an oligo(dT) primer (Invitrogen). qPCR was performed using the following primers: SFRP2 sense, 5'AAG CCT GCA AAA ATA AAA ATG ATG; SFRP2 antisense, 5'TGT AAA TGG TCT TGC TCT TGG TCT (annealing at 57.4° C.); GATA4 sense, 5'GGC CGC CCG ACA CCC CAA TCT; GATA4 antisense, 5' ATA GTG ACC CGT CCC ATC TCG (annealing at 64° C.). qPCR was performed in a MyiQ single color real-time PCR machine (Bio-Rad, Hercules, Calif.) with GAPDH as an internal control.

Determination of Cell Viability.

Calu-6 human anaplastic non-small cell lung carcinoma cells were maintained in culture using RPMI medium plus 10% fetal bovine serum. For the (3-(4,5-dimethylthiazol-2-yl)-5-(3-carboxymethoxyphenyl)-2-(4-sulfophenyl)-2H-tetrazolium) (MTS) reduction assay, 4000 cells/well were seeded in 100 μl medium in a 96-well plate and the cells were allowed to attach at 37° C. in 5% $CO_2$ for one day. The medium was aspirated and cells were treated with 100 μl of fresh medium containing appropriate concentrations of each test compound. The cells were incubated for 4 days at 37° C. in 5% $CO_2$. After 4 days 20 μL of the MTS reagent solution (Promega CellTiter 96 Aqueous One Solution Cell Proliferation Assay) was added to the medium. The cells were incubated for another 2 hours at 37° C. under 5% $CO_2$ environment. Absorbance was measured at 490 nm on a microplate reader equipped with SOFTmax PRO 4.0 software to determine the cell viability.

TABLE 2

| Entry | Compound | LSD1 % activity remaining at 10 μM | H3K4me2 Fold Increase (24 h) | H3K4me2 Fold Increase (48 h) |
|---|---|---|---|---|
| 1 | 2d | 0% | 5.1 (10 μM) | 5.1 (10 μM) |
| 2 | ± trans-2-phenylcyclopropylamine<br>Chemical Formula: $C_9H_{12}ClN$<br>Molecular Weight: 169.65 | 81.6 | | |
| 3 | Pargyline<br>Chemical Formula: $C_{11}H_{14}ClN$<br>Molecular Weight: 195.69 | 31.2 | 1.83 (10 μM) | 1.29 (5 μM)<br>0.91 (10 μM) |
| 4 | | 68.2 | 1.43 (5 μM) | 1.16 (10 μM) |
| 5 | | 82.7 | 1.51 (10 μM) | 1.16 (10 μM) |
| 6 | | 76.0 | 0.75 (5 μM)<br>1.09 (10 μM) | 1.94 (5 μM)<br>1.49 (10 μM) |
| 7 | | 68.3 | | |
| 8 | | 89.6 | 0.9 (10 μM) | 1.6 (10 μM) |
| 9 | | 99.9 | 1.1 (10 μM) | 1.1 (10 μM) |

TABLE 2-continued

| Entry | Compound | LSD1 % activity remaining at 10 μM | H3K4me2 Fold Increase (24 h) | H3K4me2 Fold Increase (48 h) |
|---|---|---|---|---|
| 10 | 2-OCH₃ phenyl derivative | 84.6 | 0.93 (5 μM)<br>1.45 (10 μM) | 1.4 (5 μM)<br>1.09 (10 μM) |
| 11 | 2-NO₂ phenyl derivative | 98.0 | 0.2 (5 μM)<br>0.4 (10 μM) | 0.4 (5 μM)<br>0.4 (10 μM) |
| 12 | 2-CH₃ phenyl derivative | 100 | 0.0 (5 μM)<br>0.0 (10 μM) | 6.2 (5 μM)<br>5.1 (10 μM) |
| 13 | 2-OH phenyl derivative | 69.9% | 561.5 (5 μM)<br>837.5 (10 μM) | 3.7 (5 μM)<br>2.7 (10 μM) |
| 14 | 2-SH phenyl derivative | 91.4 | 665.4 (5 μM)<br>81.8 (10 μM) | 1.4 (5 μM)<br>2.1 (10 μM) |
| 15 | 2-CH₂CH₃ phenyl derivative | 100 | 1591.0 (5 μM)<br>3791.7 (10 μM) | 5.4 (5 μM)<br>2.5 (10 μM) |
| 16 | 2-isopropyl phenyl derivative | 100 | 953.0 (5 μM)<br>7658.7 (10 μM) | 0.8 (5 μM)<br>0.8 (10 μM) |
| 17 | 2-phenyl phenyl (biphenyl) derivative | 100 | 1398.6 (5 μM)<br>2422.5 (10 μM) | 7.7 (5 μM)<br>0.5 (10 μM) |
| 18 | 2-OCH₂CH₃ phenyl derivative | 89.6 | 644.6 (5 μM)<br>280.3 (10 μM) | 2.0 (5 μM)<br>13.4 (10 μM) |

TABLE 2-continued

| Entry | Compound | LSD1 % activity remaining at 10 μM | H3K4me2 Fold Increase (24 h) | H3K4me2 Fold Increase (48 h) |
|---|---|---|---|---|
| 19 | 2-phenoxyphenyl amide oxime | 95.2 | 0.0 (5 μM) 3.4 (10 μM) | 0.0 (5 μM) 3.1 (10 μM) |
| 20 | 2-CF3 phenyl amide oxime | 100 | 0.0 (5 μM) 176.8 (10 μM) | 0.0 (5 μM) 13.1 (10 μM) |
| 21 | 2-Cl phenyl amide oxime | 100 | 0.0 (5 μM) 11.0 (10 μM) | 49.0 (5 μM) 0.0 (10 μM) |
| 22 | 2-Br phenyl amide oxime | 99.8 | 39.9 (5 μM) 74.5 (10 μM) | 6.7 (5 μM) 4.9 (10 μM) |
| 23 | 2-carboxamide phenyl amide oxime | 97.9 | 1.5 (5 μM) 1.7 (10 μM) | 0.0 (5 μM) 11.5 (10 μM) |
| 24 | 2-ethoxycarbonyl phenyl amide oxime | 83.4 | 15.9 (5 μM) 8.6 (10 μM) | 3.1 (5 μM) 1.4 (10 μM) |
| 25 | 2,4-difluorophenyl amide oxime | 100 | 0.9 (10 μM) | 7.1 (10 μM) |
| 26 | 2,3-difluorophenyl amide oxime | 100 | 7.1 (10 μM) | 0.2 (10 μM) |
| 27 | 4-fluorophenyl amide oxime | 74.7 | 7.0 (10 μM) | 1.2 (10 μM) |

TABLE 2-continued
| Entry | Compound | LSD1 % activity remaining at 10 μM | H3K4me2 Fold Increase (24 h) | H3K4me2 Fold Increase (48 h) |
|---|---|---|---|---|
| 28 | 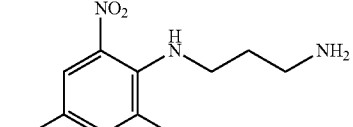 | 94.5% | 0.8 (10 μM) | 1.1 (10 μM) |
| 29 | 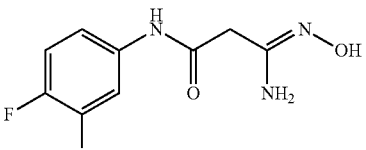 | 100 | 3.1 (10 μM) | 21.4 (10 μM) |
| 30 | 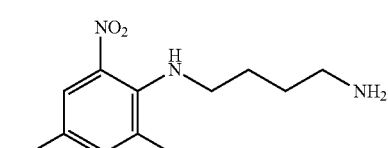 | 86.6 | 0.9 (10 μM) | 0.8 (10 μM) |
| 31 | 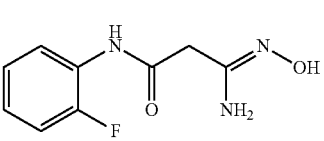 [SMILES: N/C(CC(=O)Nc1ccccc1F)=N\O] | 94.4 | 0.7 (10 μM) | 12.44 (10 μM) |
| 32 | 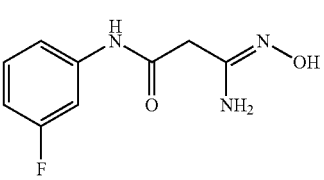 [SMILES: N/C(CC(=O)Nc1cccc(F)c1)=N\O] | 100 | 1.0 (10 μM) | 0.6 (10 μM) |
| 33 | 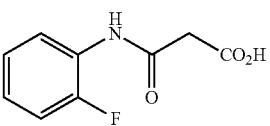<br>MW: 197.16 | 98.2 | 1.81 (5 μM)<br>1.50 (10 μM) | 3.15 (5 μM)<br>1.09 (10 μM) |
| 34 | 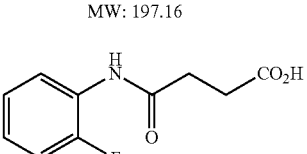<br>MW: 211.19 | 92.6 | | |
| 35 | 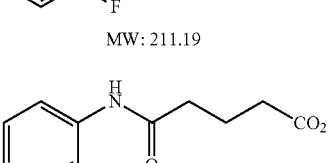<br>MW: 225.22 | 100 | | |
| 36 | 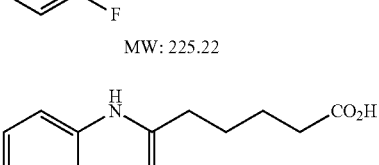<br>MW: 239.24 | 76.4 | | |

TABLE 2-continued
| Entry | Compound | LSD1 % activity remaining at 10 μM | H3K4me2 Fold Increase (24 h) | H3K4me2 Fold Increase (48 h) |
|---|---|---|---|---|
| 37 | 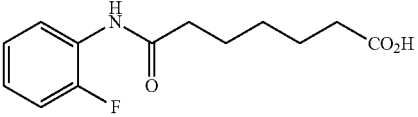<br>MW: 253.27 | 95.9 | | |
| 38 | 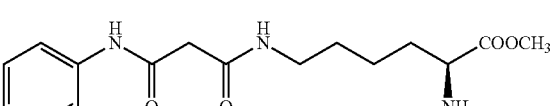 | 88.4 | 0.3 (5 μM)<br>0.2 (10 μM) | 0.7 (5 μM)<br>5.6 (10 μM) |
| 39 | 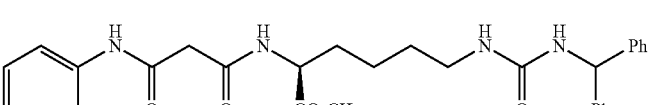<br>MW: 548.61 | 100 | | |
| 40 | 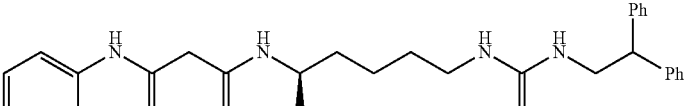<br>MW: 562.63 | 100 | | |
| 41 | 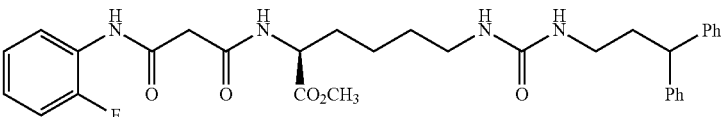<br>MW: 576.66 | 100 | | |
| 42 | 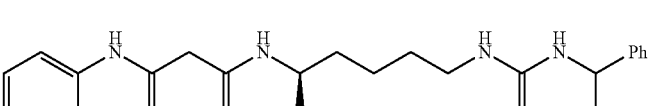<br>MW: 564.67 | 100 | 49.1 (5 μM)<br>60.6 (10 μM) | 0.5 (5 μM)<br>3.0 (10 μM) |
| 43 | 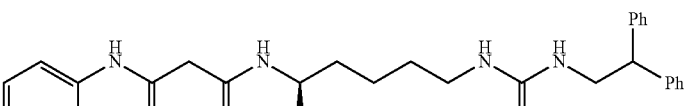<br>MW: 578.70 | 100 | | |
| 44 | 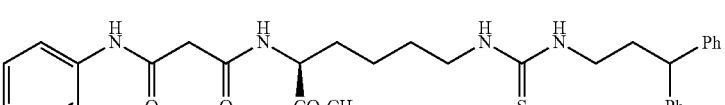<br>MW: 592.72 | 100 | | |

TABLE 2-continued

| Entry | Compound | LSD1 % activity remaining at 10 μM | H3K4me2 Fold Increase (24 h) | H3K4me2 Fold Increase (48 h) |
|---|---|---|---|---|
| 45 | MW: 505.49 | 84.1 | | |
| 46 | MW: 467.44 | 90.4 | | |
| 47 | MW: 519.52 | 92.4 | | |
| 48 | MW: 533.55 | 100 | | |
| 49 | MW: 547.57 | 100 | | |
| 50 | MW: 561.60 | 100 | | |

What is claimed is:

1. A compound of formula II,

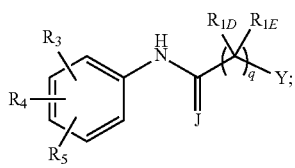

wherein
Y is

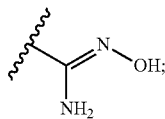

J is O;
$R_3$ is nitro, hydroxy, thio, $C(O)NR_AR_B$, or $C(O)NH_2$;
$R_4$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;
$R_5$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;
wherein $R_3$ is ortho substituted;
each $R_{1D}$ or $R_{1E}$, is independently H, alkyl, aryl, carbocyclic, heterocyclic, alkoxy, or halo, each of which is optionally substituted;
$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen; and
q is 1, 2, 3, 4, 5, 6, or 7.

2. The compound of claim 1, wherein q is 1.

3. The compound of claim 1, wherein $R_3$ is nitro, hydroxy, thio, or $C(O)NH_2$.

4. A pharmaceutical composition comprising a therapeutically effective amount of a compound of claim 1 or a pharmaceutically acceptable salt, solvate or hydrate thereof, in combination with a pharmaceutically acceptable carrier or excipient.

5. A kit comprising an effective amount of a compound of claim 1 in unit dosage form, together with instructions for administering the compound to a subject suffering from or susceptible to a LSD1-related disease.

6. The compound of claim 1, of formula II-A,

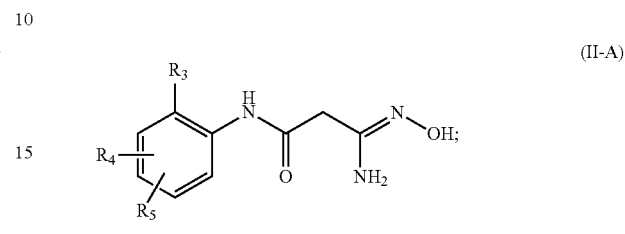

wherein
$R_3$ is nitro, hydroxy, thio, $C(O)NR_AR_B$, or $C(O)NH_2$;
$R_4$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$;
$R_5$ is H, alkyl, aryl, carbocyclic, heterocyclic, aralkyl, alkoxy, aryloxy, haloalkyl, or halo, each of which is optionally substituted, nitro, hydroxy, thio, $C(O)NR_AR_B$, or $C(O)OR_A$; and
$R_A$ and $R_B$ are each independently selected at each occurrence from the following: optionally substituted alkyl, optionally substituted alkenyl or optionally substituted alkynyl, each containing 0, 1, 2, or 3 heteroatoms selected from O, S, or N; optionally substituted aryl; optionally substituted heteroaryl; optionally substituted heterocyclic; optionally substituted carbocyclic; or hydrogen.

7. The compound of claim 1, selected from the following:

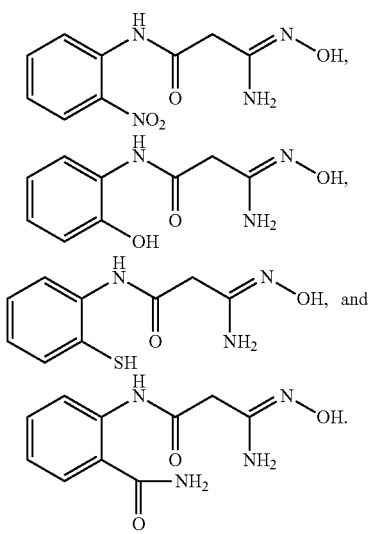

* * * * *